United States Patent
Noji et al.

(10) Patent No.: US 10,451,619 B2
(45) Date of Patent: *Oct. 22, 2019

(54) SUBSTANCE SEALING METHOD AND TARGET MOLECULE DETECTING METHOD

(71) Applicant: JAPAN SCIENCE AND TECHNOLOGY AGENCY, Kawaguchi-shi, Saitama (JP)

(72) Inventors: Hiroyuki Noji, Tokyo (JP); Lisa Yamauchi, Tokyo (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/321,312

(22) PCT Filed: Jul. 1, 2015

(86) PCT No.: PCT/JP2015/003310
§ 371 (c)(1),
(2) Date: Dec. 22, 2016

(87) PCT Pub. No.: WO2016/006208
PCT Pub. Date: Jan. 14, 2016

(65) Prior Publication Data
US 2017/0176430 A1 Jun. 22, 2017

(30) Foreign Application Priority Data
Jul. 8, 2014 (JP) .................................. 2014-140700

(51) Int. Cl.
*G01N 33/543* (2006.01)
*C12Q 1/04* (2006.01)
(Continued)

(52) U.S. Cl.
CPC ......... *G01N 33/54393* (2013.01); *C12Q 1/04* (2013.01); *C12Q 1/68* (2013.01);
(Continued)

(58) Field of Classification Search
CPC ......... G01N 33/54393; G01N 33/5308; C12M 1/00
See application file for complete search history.

(56) References Cited

U.S. PATENT DOCUMENTS

| 7,214,540 B2 | 5/2007 | DeLucas |
| 9,329,174 B2 | 5/2016 | Noji et al. |

(Continued)

FOREIGN PATENT DOCUMENTS

| CN | 1862260 A | 11/2006 |
| CN | 101947124 A | 1/2011 |

(Continued)

OTHER PUBLICATIONS

China Patent and Trademark Office (China) "Office Action" and "Search Report," issued in Chinese Patent Application No. 201280012033.7, which is a Chinese counterpart application to U.S. Appl. No. 14/003,509, dated Feb. 13, 2014.

(Continued)

*Primary Examiner* — Narayan K Bhat

(57) ABSTRACT

As a technique for efficiently sealing many substances, such as beads, nucleic acid, protein, virus, cells, and lipid membrane complex, into an array, the present invention provides a method for sealing a substance, including: (i) a step of introducing a first solvent containing a substance on a substrate on which a plurality of receptacles capable of storing the substance are formed separated from each other by a side wall; and (ii) a step of introducing a second solvent having a greater specific gravity than that of the first solvent onto the first solvent, the step (ii) being carried out after the step (i).

5 Claims, 2 Drawing Sheets

(51) Int. Cl.

| | |
|---|---|
| *C12Q 1/68* | (2018.01) |
| *C12Q 1/70* | (2006.01) |
| *G01N 37/00* | (2006.01) |
| *G01N 35/10* | (2006.01) |
| *G01N 21/64* | (2006.01) |
| *G01N 33/53* | (2006.01) |

(52) U.S. Cl.

CPC ........... *C12Q 1/70* (2013.01); *G01N 21/6428* (2013.01); *G01N 33/5308* (2013.01); *G01N 33/543* (2013.01); *G01N 33/54313* (2013.01); *G01N 35/10* (2013.01); *G01N 37/00* (2013.01); *G01N 2021/6439* (2013.01)

(56) References Cited

U.S. PATENT DOCUMENTS

| | | |
|---|---|---|
| 2004/0208792 A1 | 10/2004 | Linton et al. |
| 2006/0254933 A1 | 11/2006 | Adachi et al. |
| 2009/0166206 A1 | 7/2009 | Hattori |
| 2009/0246782 A1 | 10/2009 | Kelso et al. |
| 2009/0280251 A1 | 11/2009 | De Guzman et al. |
| 2010/0022414 A1 | 1/2010 | Link et al. |
| 2011/0065086 A1 | 3/2011 | Bruno |
| 2011/0172118 A1 | 7/2011 | Kain |
| 2011/0212848 A1 | 9/2011 | Duffy et al. |
| 2013/0204076 A1 | 8/2013 | Han et al. |
| 2013/0345088 A1 | 12/2013 | Noji et al. |
| 2015/0204785 A1 | 7/2015 | Kim et al. |

FOREIGN PATENT DOCUMENTS

| | | |
|---|---|---|
| EP | 2 685 266 A1 | 1/2014 |
| EP | 2 891 886 A1 | 7/2015 |
| JP | 2004-309405 A | 11/2004 |
| JP | 2008-111798 A | 5/2008 |
| JP | 2009-109213 A | 5/2009 |
| JP | 2009-162549 A | 7/2009 |
| JP | 2010-054335 A | 3/2010 |
| WO | 2005/021151 A1 | 3/2005 |
| WO | 2007/120241 A2 | 10/2007 |
| WO | 2008/116209 A1 | 9/2008 |
| WO | 2011/079176 A2 | 6/2011 |
| WO | 2011/109379 A1 | 9/2011 |
| WO | 2011/160430 A1 | 12/2011 |
| WO | 2012/045012 A2 | 4/2012 |
| WO | 2012/121310 A1 | 9/2012 |
| WO | 2014/034781 A1 | 3/2014 |

OTHER PUBLICATIONS

Snapshot of the website "http://www.agc.com/kagaku/shinsei/cytop/en/about.html" maintained by Asahi Glass Co., Ltd., accessed and printed on Jun. 2, 2014.

Extended European Search Report received for European Patent Application No. 12754743.8 dated Nov. 7, 2013, 5 pages.

International Search Report received for PCT Patent Application No. PCT/JP2012/055884, dated May 22, 2012, 5 pages (2 pages of English Translation and 3 pages of PCT search report).

Written Opinion received for PCT Patent Application No. PCT/JP2012/055884, dated May 22, 2012, 4 pages (Japanese Language Only) See Statement Under 37 CFR § 1.98(a) (3).

International Preliminary Report on Patentability received for PCT Patent Application No. PCT/JP2012/055884, completed on Jan. 31, 2013, 11 pages (4 pages of English Translation and 7 pages of IPRP).

Rissin et al., "Single-Molecule Enzyme-Linked Immunosorbent Assay Detects Serum Proteins at Subfemtomolar Concentrations", Nature Biotechnology, vol. 28, No. 6, Jun. 2010, pp. 595-599.

Sakakihara et al., "A Single-Molecule Enzymatic Assay in a Directly Accessible Femtoliter Droplet Array", The Royal Society of Chemistry, Lab Chip, vol. 10, 2010, pp. 3355-3362.

Chambers: Dictionary of Science and Technology, general editor Professor Peter M B Walker, CBE, FRSE, Chambers Harrap Publishers Ltd. p. 1150 (1999).

Snapshot of the website "http://www.sigmaaldrich.com/catalog/product/aldrich/469629?lang=en&region=US" maintained by Sigma-Aldrich Co. LLC, accessed and printed on Aug. 26, 2014.

Snapshot of the website "http://www.sigmaaldrich.com/catalog/product/aldrich/469610?lang=en&region=US" maintained by Sigma-Aldrich Co. LLC, accessed and printed on Aug. 26, 2014.

S. Capizzi and J. Schwartzbrod, "Surface properties of Ascaris suum eggs: hydrophobic potential and Lewis acid-base interactions", Colloids and Surfaces B: Biointerfaces, vol. 22, pp. 99-105 (2001), Elsevier Science B.V.

Andrew D. Griffiths and Dan S. Tawfik, "Directed evolution of an extremely fast phosphotriesterase by in vitro compartmentalization", The EMBO Journal, vol. 22, No. 1, pp. 24-35 (2003).

Jacqueline R. Retting and Albert Folch, "Large-Scale Single-Cell Trapping And Imaging Using Microwell Arrays", Analytical Chemistry, vol. 77, pp. 5628-5634 (2005), American Chemical Society.

Yannick Rondelez et al., "Microfabricated arrays of femtoliter chambers allow single molecule enzymology", Nature Biotechnology, vol. 23, No. 3, pp. 361-365 (Mar. 2005).

United States Patent and Trademark Office, Office Action, issued in U.S. Appl. No. 14/003,509, with a notification date of Dec. 11, 2014, 19 pages.

International Search Report received for PCT Patent Application No. PCT/JP2015/003310 dated Aug. 11, 2015, 3 pages.

United States Patent and Trademark Office, Office Action, issued in U.S. Appl. No. 14/003,509, with a notification date of Jun. 29, 2015, 19 pages.

United States Patent and Trademark Office, Office Action, issued in U.S. Appl. No. 14/003,509, with a notification date of Mar. 7, 2014, 11 pages.

United States Patent and Trademark Office, Office Action, issued in U.S. Appl. No. 14/003,509, with a notification date of Jul. 1, 2014, 9 pages.

United States Patent and Trademark Office, "Non-Final Office Action", issued in U.S. Appl. No. 14/513,660, with a notification date of May 19, 2016, 27 pages.

United States Patent and Trademark Office, "Final Office Action", issued in U.S. Appl. No. 14/513,660, with a notification date of Oct. 13, 2016, 29 pages.

Alan U. Larkman, An Ultrastructural Study of Oocyte Growth Within the Endoderm and Entry Into the Mesoglea in Actinia fragacea (Cnidaria, Anthozoa), Journal of Morphology, vol. 178, Issue 2, pp. 155-177 (1983).

United States Patent and Trademark Office, "Non-Final Office Action", issued in U.S. Appl. No. 15/082,195, with a notification date of May 16, 2016, 17 pages.

United States Patent and Trademark Office, "Advisory Action", issued in U.S. Appl. No. 14/003,509, with a notification date of Sep. 8, 2014, 5 pages.

United States Patent and Trademark Office, "Advisory Action", issued in U.S. Appl. No. 14/513,660, with a notification date of Dec. 19, 2016, 9 pages.

United States Patent and Trademark Office, "Non-Final Office Action", issued in U.S. Appl. No. 14/513,660, with a notification date of Mar. 30, 2017, 22 pages.

"Sigma data sheet, Down loaded from the Internet [www.sigma-aldrich.com]; printed on Mar. 26, 2017, p. 1" provided by the United States Patent and Trademark Office with the Non-Final Office Action issued in U.S. Appl. No. 14/513,660 with a notification date of Mar. 30, 2017.

European Patent Office, "Extended European Search Report," issued in European Patent Application No. 15 819 235.1, dated Dec. 13, 2017.

European Patent Office, Office Communication, issued in European Patent Application No. 15 819 235.1, dated Sep. 3, 2018.

SUBSTANCE SEALING METHOD AND TARGET MOLECULE DETECTING METHOD

CROSS REFERENCE TO RELATED APPLICATIONS

This patent application is a U.S. national stage application under 35 U.S.C. § 371 of International Patent Application No. PCT/JP2015/003310 filed on Jul. 1, 2015, which claims the benefit of foreign priority to Japanese Patent Application No. JP 2014-140700 filed on Jul. 8, 2014. The International Application was published in Japanese on Jan. 14, 2016, as International Publication No. WO 2016/006208 A1 under PCT Article 21(2).

FIELD OF THE INVENTION

The present invention relates to a method for sealing substances and detecting a target molecule.

BACKGROUND OF THE INVENTION

There has been known a single-molecule assay as a method for carrying out various assays by observing biomolecules such as proteins and nucleic acids in such a manner that the biomolecules are individually identified. In order to carry out the single-molecule assay, there have been known some methods.

Patent Literature 1 discloses a micro chamber for detecting single-molecule enzyme activity. This micro chamber includes a container part into which a liquid droplet can be sealed and which has capacity of storing a liquid droplet of up to 1000 fL (femtoliters). The container part is made of a recess provided in at least one of a first member and a second member which are bonded to each other. According to Patent Literature 1, an enzyme reaction is carried out in the liquid droplet. With such a configuration, the enzyme reaction can be performed with a high concentration of the reaction products, even if the number of molecules of the reaction products is quite small. Thus, it is possible to detect an activity of one molecule of enzyme.

Non-Patent Literature 1 discloses a method for carrying out a single-molecule enzyme assay by use of an array where a liquid droplet is covered with oil, in a femtoliter-order, and accessible directly from the outside. This array includes a hydrophilic region pattern made of a hydrophilic surface on which a hydrophobic region having a height of 17 nm is provided.

Non-Patent Literature 2 discloses a method for detecting a protein by a single-molecule Enzyme-Linked ImmunoSorbent Assay (ELISA). According to this method, a very small amount of proteins are captured by minute beads covered with protein-specific antibodies, and complexes of the beads and the proteins are fluorescence-labeled. Then, beads including the complexes are introduced into a reaction chamber by centrifugal force. Thereafter, the number of beads having captured the proteins is counted. In this manner, the proteins are quantitatively assayed.

CITATION REFERENCES

Patent Literatures

[Patent Literature 1] Japanese Patent Application Publication, Tokukai, No. 2004-309405 A

Non-Patent Literatures

[Non-Patent Literature 1] S. Sakakihara et al., Lab Chip, 2010, 10, 3355-3362
[Non-Patent Literature 2] David M Rissin et al., Nature Biotechnology: doi: 10.1038/nbt.1641

BRIEF SUMMARY OF THE INVENTION

Technical Problem

In order to detect, e.g., disease markers of low concentration for early detection of diseases, infectious diseases, and the like, there is a demand for biosensing techniques developed to have higher sensitivities. For example, in a case where one million cancer cells included in a tumor having a volume of 1 $mm^3$ secrete marker proteins (100 molecules per cell) into 5-liter blood, a concentration of the proteins in the blood is approximately 30 aM. A technique capable of detecting target molecules of such quite low concentration is needed.

A possible method for detecting such the target molecules may be the one for detecting the target molecules by the above-mentioned single-molecule enzyme assay at a single molecule level sensitivity. Specifically, such the method is carried out by (i) sealing the target molecule specifically into a femtoliter-order liquid droplet (very small liquid droplet), (ii) linking the target molecule to a substance such as an enzyme-labeled antibody, and (iii) detecting an activity of the enzyme labeling the antibody in the above-mentioned manner. The sealing of the target molecule specifically into the very small liquid droplet may be carried out by a method using, e.g., a bead labeled with a substance such as another antibody for specifically binding to the target molecule. In this method, after the bead is bound to the target molecule, the bead is sealed into the very small solution droplet.

Incidentally, in order to efficiently detect target molecules which are contained in a solution only in a very small amount e.g., approximately 30 aM target molecules as described above, it is necessary to prepare a large number of very small liquid droplet arrays, as many as approximately one million, and to cause the arrays to capture the beads.

However, according to the method disclosed by Non-Patent Literature 2, the beads need to be introduced into arrays by strong centrifugal force, and therefore much time and efforts are required. Further, the number of arrays used in the method of Non-Patent Literature 2 is approximately fifty thousand. Therefore, the method of Non-Patent Literature 2 is quite difficult to be applied to the case requiring approximately one million arrays. Thus, with the method of Non-Patent Literature 2, it is difficult to efficiently seal a large number of beads into the arrays. Incidentally, none of Patent Literature 1 and Non-Patent Literature 1 discloses any method for solving such the problem.

In view of this, the present invention has an object to provide a technique for efficiently sealing a large number of substances, such as beads, nucleic acid, protein, virus, cells, and lipid membrane complex, into an array.

Solution to Problem

In order to attain the above object, the present invention provides the following method for sealing a substance and the like.

[1] A method for sealing a substance, including: (i) a step of introducing a first solvent containing a substance on a substrate on which a plurality of receptacles capable of storing the substance are formed separated from each other by a side wall; and (ii) a step of introducing a second solvent having a greater specific gravity than that of the first solvent onto the first solvent, the step (ii) being carried out after the step (i).

[2] The method according to [1], wherein at least one of the first solvent and the second solvent contains a surfactant.

[3] The method according to [2], wherein the surfactant in the first solvent has a concentration of 0.01% to 1%.

[4] The method according to [2] or [3], wherein the surfactant is TWEEN 20 or Triton X-100.

[5] The method according to any one of [1] to [4], wherein the second solvent is at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixture including the at least one.

[6] The method according to any one of [1] to [5], wherein the first solvent is at least one selected from the group consisting of water, hydrophilic alcohol, hydrophilic ether, ketone, nitrile solvents, dimethyl sulfoxide, and N,N-dimethylformamide, or is a mixture including the at least one.

[7] The method according to [5] or [6], wherein the side wall has a hydrophobic upper surface including a fluorocarbon polymer resin and the second solvent is a polymer having a perfluorocarbon structure.

[8] The method according to [7], wherein the fluorocarbon polymer resin is amorphous fluorocarbon resin.

[9] The method according to any one of [1] to [8], wherein a region including the receptacles of the substrate is opened to the outside.

[10] The method according to any one of [1] to [9], wherein the substance is one or more selected from beads, nucleic acid, protein, virus, cells, and lipid membrane complex.

[11] A method for detecting a target molecule, including: (i) a step of reacting beads specifically capturing target molecules with the target molecules; a step of carrying out, by use of the beads, a method recited in any one of [1] to [9], the step (ii) being carried out after the step (i); and a step of determining whether or not any one of beads having captured the target molecule is stored in each of the plurality of the receptacles, the step (iii) being carried out after the step (ii).

[12] The method according to [11], wherein the beads are such beads to which molecules specifically bindable to the target molecules are bound.

[13] A method for sealing a substance in receptacles provided on a substrate by introducing a hydrophilic solvent containing the substance into the receptacles and coating the hydrophilic solvent containing the substance introduced into the receptacles with a hydrophobic solvent, including: (i) a step of introducing a hydrophilic solvent containing the substance on a substrate on which a plurality of receptacles capable of storing the substance are formed separated from each other by a side wall; and (ii) a step of introducing a hydrophobic solvent having a greater specific gravity than that of the hydrophilic solvent onto the hydrophilic solvent, the step (ii) being carried out after the step (i).

[14] The method according to [13], wherein at least one of the hydrophilic solvent and the hydrophobic solvent contains a surfactant.

[15] The method according to [14], wherein the surfactant in the hydrophilic solvent has a concentration of 0.01% to 1%.

[16] The method according to [14] or [15], wherein the surfactant is TWEEN 20 or Triton X-100.

[17] The method according to any one of [13] to [16], wherein the hydrophobic solvent is at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixture including the at least one.

[18] The method according to any one of [13] to [17], wherein the hydrophilic solvent is at least one selected from the group consisting of water, hydrophilic alcohol, hydrophilic ether, ketone, nitrile solvents, dimethyl sulfoxide, and N,N-dimethylformamide, or is a mixture including the at least one.

[19] The method according to [17] or [18], wherein the side wall has a hydrophobic upper surface including a fluorocarbon polymer resin and the hydrophobic solvent is a polymer having a perfluorocarbon structure.

[20] The method according to [19], wherein the fluorocarbon polymer resin is amorphous fluorocarbon resin.

[21] The method according to any one of [13] to [20], wherein a region including the receptacles of the substrate is opened to the outside.

[22] The method according to any one of [13] to [21], wherein the substance is one or more selected from beads, nucleic acid, protein, virus, cells, and lipid membrane complex.

[23] A method for detecting a target molecule, including: (i) a step of reacting beads specifically capturing target molecules with the target molecules; (ii) a step of carrying out, by use of the beads, a method recited in any one of [13] to [21], the step (ii) being carried out after the step (i); and (iii) a step of determining whether or not any one of beads having captured the target molecule is stored in each of the plurality of the receptacles, the step (iii) being carried out after the step (ii).

[22] The method according to [21], wherein the beads are such beads to which molecules specifically bindable to the target molecules are bound.

Advantageous Effects of Invention

The use of the method for sealing a substance according to the present invention makes it possible to efficiently seal many substances, such as beads, nucleic acid, protein, virus, cells, and lipid membrane complex, into an array, thereby contributing to a technique by which target molecules of low concentration are detectable with high sensitivity.

DETAILED DESCRIPTION OF THE INVENTION

A preferred mode for carrying out the present invention will be described below with reference to the drawings. The embodiments described below are intended only to show an example of an exemplary embodiment of the present invention, but the scope of the present invention is not intended to be construed in a limiting sense thereby.

In the method for sealing a substance according to the present invention, the substance sealed in receptacles provided on a substrate may be beads, nucleic acid, protein, virus, cells, lipid membrane complex, or the like; however, the following embodiment will be described using beads as an example.

1. Method for Sealing Beads

Figure 1:
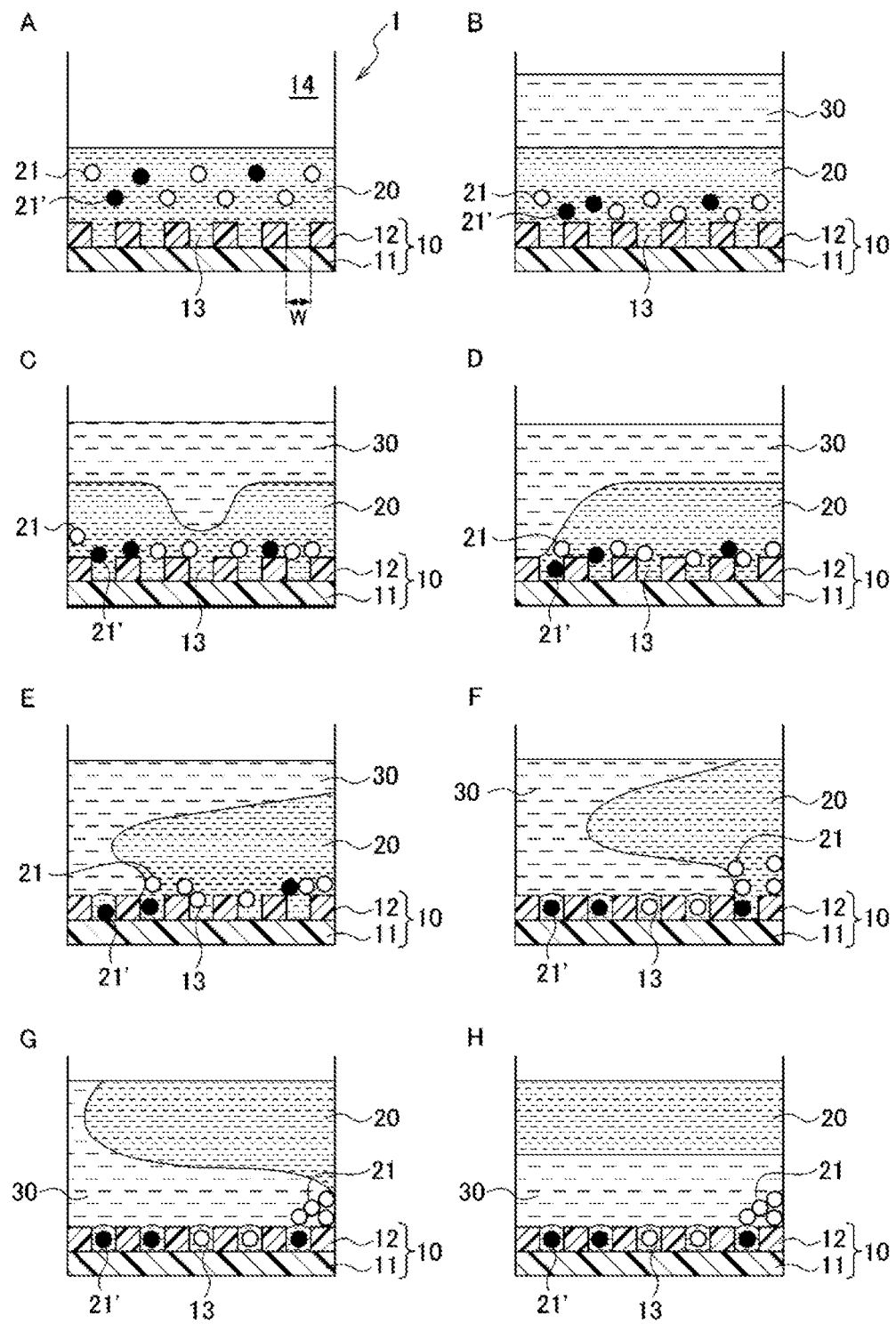
FIG. 1 is a series of views schematically illustrating the procedure of the method for sealing a substance according to the present invention, which show lateral cross-sectional views of an array 1.

With reference to FIG. 1, the following describes a method for sealing beads according to the present invention. FIG. 1 is a series of views schematically illustrating the procedure of the method for sealing beads according to the present invention, which show lateral cross-sectional views of an array 1.

The present embodiment deals with a case will be described where beads 21 and 21' are sealed into the array 1 including a substrate 10. The substrate 10 includes a plurality of receptacles 13 each of which is capable of storing only one of the beads 21 and 21' and which are separated from each other by a side wall 12 having a hydrophobic upper surface.

Here, "bead" is used synonymously with "particle" and is a technical term commonly used in the art. The shape of the bead is not particularly limited; however, it is typically spherical. The material of the bead is also not particularly limited and may be glass, silica gel, polystyrene, polypropylene, membrane, magnetic material, or the like. Specific examples of the material include cellulose, cellulose derivatives, acrylic resin, glass, silica gel, polystyrene, gelatin, polyvinylpyrrolidone, copolymers of vinyl and acrylamide, polystyrenes crosslinked with divinylbenzene and the like, polyacrylamide, latex gel, polystyrene dextran, rubber, silicon, plastics, nitrocellulose, cellulose, natural sponge, silica gel, glass, metal plastics, cellulose, crosslinked dextran (Sephadex (Registered Trademark)), and agarose gel (Sepharose (Registered Trademark)). The beads may be porous. The beads preferably have an average particle diameter of 5 μm or less, for example, approximately 1 μm to 4 μm. With this, the beads can be efficiently sealed into the array, and the array can achieve high density. Note that the term "average particle diameter" herein refers to a value obtained as a result of measurement of the beads by means of electron microscope observation or dynamic light scattering.

The present embodiment describes, but is not particularly limited to, a case of using beads specifically capturing target molecules. In the present embodiment, the beads to be sealed are a mixture of the beads 21, which have not captured the target molecules yet, and the beads 21', which have captured the target molecules.

For example, it is possible to use, as the beads specifically capturing the target molecules, beads being bound to a molecule for specifically capturing the target molecule. The molecule for specifically capturing the target molecule may be bound to a modification group on a surface of the bead, e.g., via a linker. For example, the present invention may be configured such that the molecule for specifically capturing the target molecule is covalently bonded to an amino group on a surface of an amino group-modified bead via a crosslinker having N-hydroxysuccinimide and/or the like.

The "target molecule" refers to a molecule which is to be detected (targeted molecule). Specifically, the "target molecule" herein refers to a molecule which is to be detected by causing the bead to capture the molecule. Examples of the target molecule encompass (i) biomolecules, such as a protein, a nucleic acid, and sugar, and (ii) virus particles themselves.

The molecule for specifically capturing a target molecule (hereinafter such molecule is also referred to as a "target capturing molecule") may be chosen according to the target molecule. Examples of the target capturing molecule encompass a protein, an antibody, and a nucleic acid. Preferably, one bead is bounded to hundred thousand or more target capturing molecules. For example, in a case where the target capturing molecule is an antibody, the target capturing molecule has a dissociation constant in nM order or so. However, with the above-mentioned configuration, it is possible to cause the reaction between the beads and the target molecules with a sufficiently high concentration of the target capturing (for example, in a case where the concentration of the beads is $8*10^6$ particles/mL, the concentration of the target capturing molecules is approximately 1 nM).

The method for sealing beads according to the present embodiment includes a step of beads introduction, a step of deaeration, and a step of beads storing. Each of these steps will be described in detail below.

[Step of Beads Introduction]

The following describes the step of beads introduction with reference to FIG. 1A.

The step of beads introduction is a step of introducing a first solvent 20 containing the beads 21 and 21' onto the substrate 10. The method for introducing the first solvent 20 is not particularly limited; however, a method can be adopted which involves using a region 14 including the receptacles 13 of the substrate 10 as an opened well which is opened to the outside to introduce the first solvent 20 from the opening into the well.

The first solvent 20 is preferably a hydrophilic solvent; preferably used as it is, for example, at least one selected from the group consisting of water, hydrophilic alcohol, hydrophilic ether, ketone, nitrile solvents, dimethyl sulfoxide (DMSO), and N,N-dimethylformamide (DMF) or is a mixture including the at least one. Examples of hydrophilic alcohol encompass ethanol, methanol, propanol, and glycerin. Examples of hydrophilic ether encompass tetrahydrofuran, polyethylene oxide, and 1,4-dioxane. Examples of ketones encompass acetone and methyl ethyl ketone. Examples of nitrile solvents encompass acetonitrile.

The first solvent 20 preferably contains a surfactant. In the step of beads storing to be described next, a second solvent 30 having a greater specific gravity than that of the first solvent 20 is introduced onto the first solvent 20 (see FIG. 1B), followed by performing substitution based on the difference in specific gravity between the first solvent 20 and the second solvent 30 to move the second solvent 30 to the lower layer of the first solvent 20 (see FIG. 1H). On this occasion, a surfactant can be added to the first solvent 20 and/or the second solvent 30 to promote the substitution between the first solvent 20 and the second solvent 30.

The surfactant is not particularly limited; however, examples thereof encompass TWEEN 20 (CAS No. 9005-64-5, polyoxyethylene sorbitan monolaurate) and Triton X-100 (CAS No. 9002-93-1, general name: polyethylene glycol mono-4-octylphenyl ether (n≈10)). The concentration of the surfactant added to the first solvent 20 is not particularly limited; however, it is preferably 0.01 to 1%.

In addition, an anionic surfactant, a cationic surfactant, a nonionic surfactant, a zwitterionic surfactant, a surfactant derived from nature, or the like can be widely used as the surfactant.

The anionic surfactant is classified, for example, into a carboxylic type, a sulfate type, a sulfonic type, and a phosphate type. Specific examples thereof encompass sodium dodecyl sulfate, sodium laurate, sodium α-sulfo fatty acid methyl ester, sodium dodecylbenzenesulfonate, and sodium dodecylethoxylate sulfate; among these, sodium dodecylbenzenesulfonate is preferably used.

The cationic surfactant is classified, for example, into a quaternary ammonium salt type, an alkylamine type, and a heterocyclic amine type. Specific examples thereof encompass stearyltrimethylammonium chloride, distearyldimethylammonium chloride, didecyldimethylammonium chloride, cetyltripyridinium chloride, and dodecyldimethylbenzylammonium chloride.

Examples of the nonionic surfactant encompass polyoxyethylene alkyl ethers, polyoxyethylene hydrogenated castor oils, polyoxyethylene mono fatty acid esters, polyoxyethylene sorbitan mono fatty acid esters, sucrose fatty acid esters, polyglyceryl fatty acid esters, alkyl polyglucosides, and N-methylalkyl glucamides. Among those, preferred are nonionic surfactants available under the names of Triton X (Triton X-100, and the like), Pluronic (Registered Trademark) (Pluronic F-123, F-68, and the like), Tween (Tween 20, 40, 60, 65, 80, 85, and the like), Brij (Registered Trademark) (Brij 35, 58, 98, and the like), and Span (Span 20, 40, 60, 80, 83, and 85) in addition to dodecyl alcohol ethoxylate, nonylphenol ethoxylate, and lauroyl diethanol amide.

Examples of the amphoteric surfactant encompass lauryldimethyl aminoacetic acid betaine, dodecylaminomethyldimethylsulfopropyl betaine, and 3-(tetradecyldimethylaminio)propane-1-sulfonate; however, preferred examples thereof used encompass 3-[(3-cholamidopropyl)dimethylammonio]-1-propane sulfonate (CHAPS) and 3-[(3-cholamidopropyl)dimethylammonio]-2-hydroxy-1-propane sulfonate (CHAPSO).

The surfactant derived from nature is preferably, for example, lecithin or saponin. Among compounds called lecithin, preferred are specifically phosphatidylcholine, phosphatidylethanolamine, phosphatidylinositol, phosphatidylserine, phosphatidic acid, and phosphatidylglycerol. Quillaja saponin is preferable as saponin.

In addition to the beads 21 and 21', the first solvent 20 may further include, e.g., a substance for specifically detecting the target molecule captured by any of the beads 21'. Such the substance may be, for example, a fluorescent substrate which liberates a fluorescent material when decomposed by a certain enzyme bound to (i) the target molecule captured by any of the beads 21' or (ii) a molecule specifically bound to the target molecule. Examples of the molecule specifically bound to the target molecule encompass a secondary antibody and a nucleic acid. Examples of the certain enzyme encompass β-galactosidase and peroxidase. Examples of the fluorescent substrate encompass fluorescein-di-β-galactopyranoside (FDG) and Amplex Red (Registered Trademark).

[Step of Beads Storing]

The following describes the step of beads storing with reference to FIGS. 1B to 1H.

The step of beads storing is a step of introducing the second solvent 30 having a greater specific gravity than that of the first solvent 20 onto the first solvent 20. The method for introducing the second solvent 30 is not particularly limited; however, a method can be adopted which involves using the region 14 including the receptacles 13 of the substrate 10 as an opened well which is opened to the outside to introduce the second solvent 30 from the opening into the well. On this occasion, the second solvent 30 is preferably introduced so that the layer of the second solvent 30 is laminated on the layer of the first solvent 20 as shown in FIG. 1B.

The second solvent 30 may be a solvent having a greater specific gravity than that of the first solvent 20 used in the step of beads introduction. The first solvent 20 and the second solvent 30 are preferably mutually amphiphilic to a degree capable of layer substitution; however, they are required to be not compatible to each other. Too a low amphiphile between the first solvent 20 and the second solvent 30 does not produce the layer substitution between the first solvent 20 and the second solvent 30. The layer substitution between the first solvent 20 and the second solvent 30 also does not occur when the first solvent 20 and the second solvent 30 are compatible with each other. In order to prevent the mingling of the first solvent 20 and the second solvent 30, it is preferable to use a hydrophilic solvent as the first solvent 20 and a hydrophobic solvent as the second solvent 30. Like the first solvent 20, the second solvent 30 may contain a surfactant to promote the layer substitution.

Such the second solvent 30 is preferably a hydrophobic solvent; preferably used as it is, for example, at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixture including the at least one. Examples of saturated hydrocarbons encompass alkanes and cycloalkanes. Examples of alkanes encompass decane and hexadecane. Examples of unsaturated hydrocarbons encompass squalene. Examples of aromatic hydrocarbons encompass benzene and toluene. Examples of hexafluoropropylene epoxide polymers encompass Krytox 143 (from DuPont Co., Ltd.) and Krytox GPL (from DuPont Co., Ltd.). Examples of the polymer having a hydrofluoroether structure encompass Asahiklin AE3000 (from Asahi Glass Co., Ltd.) and Novec 7000 (from Sumitomo 3M Co., Ltd.). Examples of the polymer having a perfluorocarbon structure encompass Fluorinert FC-40 and Fluorinert FC-43 (from Sumitomo 3M Co., Ltd.).

The second solvent 30 introduced and laminated onto the first solvent 20 has a greater specific gravity than that of the first solvent 20 and thus moves down below the first solvent 20. Specifically, the substitution between the first solvent 20 and the second solvent 30 takes place and thereby the state in which the upper layer is the second solvent 30 with the lower layer being the first solvent 20 (see FIG. 1B) becomes a state in which the upper layer is the first solvent 20 with the lower layer being the second solvent 30 (see FIG. 1H). FIGS. 1C to G schematically show how the layer substitution occurs. In this layer substitution, the beads 21 and 21' precipitating on the bottom of the region 14 are stored in the respective receptacles 13, in which case they are forced thereinto by the second solvent 30 moving down below the first solvent 20 (see FIGS. 1D to F). As a result, the beads can be sealed with high efficiency into each of a large number of receptacles 13 which are provided on the substrate 10. In the case of using a hydrophilic solvent as the first solvent 20 and a hydrophobic solvent as the second solvent 30, droplets (liquid droplets of the first solvent 20) covered by the second solvent 30 are efficiently formed in the respective receptacles 13.

Here, preferred examples of the first solvent 20 and the second solvent 30 used in the bead sealing method according to the present invention are as in "Table 1" and "Table 2".

TABLE 1

| First solvent | Density |
| --- | --- |
| water | 1.000 g/mL at 3.98° C. (lit.) |
| methanol | 0.791 g/mL at 25° C. (lit.) |
| ethanol | 0.789 g/mL at 25° C. (lit.) |
| 1-propanol | 0.804 g/mL at 25° C. (lit.) |
| 2-propanol | 0.785 g/mL at 25° C. (lit.) |
| 1-butanol | 0.81 g/mL at 25° C. (lit.) |
| N,N-dimethylformamide | 0.944 g/mL (lit.) |
| acetonitrile | 0.786 g/mL at 25° C. (lit.) |
| acetone | 0.791 g/mL at 25° C. (lit.) |
| tetrahydrofuran | 0.889 g/mL at 25° C. (lit.) |

TABLE 2

| Second solvent | Density |
| --- | --- |
| PF-5052 | 1.700 g/mL at 25° C. |
| Fluorinert FC-72 | 1.680 g/mL at 25° C. |
| Fluorinert FC-770 | 1.790 g/mL at 25° C. |
| Fluorinert FC-3283 | 1.830 g/mL at 25° C. |
| Fluorinert FC-40 | 1.870 g/mL at 25° C. |
| Fluorinert FC-43 | 1.880 g/mL at 25° C. |
| chloroform | 1.492 g/mL at 25° C. (lit.) |
| Asahiklin AE-3000 | 1.470 g/mL at 25° C. |
| Novec 7000 | 1.400 g/mL |
| Novec 7100 | 1.520 g/mL |
| Novec 7200 | 1.430 g/mL |
| Novec 7300 | 1.660 g/mL |
| Krytox GPL-100 | 1.87 g/mL at 0° C. |
| Krytox GPL-101 | 1.89 g/mL at 0° C. |
| Krytox GPL-102 | 1.91 g/mL at 0° C. |
| Krytox GPL-103 | 1.92 g/mL at 0° C. |
| Krytox GPL-104 | 1.93 g/mL at 0° C. |
| Krytox GPL-105 | 1.94 g/mL at 0° C. |
| Krytox GPL-106 | 1.95 g/mL at 0° C. |
| Krytox GPL-107 | 1.95 g/mL at 0° C. |

In the step of beads storing, when magnetic beads are used as the beads 21 and 21', a magnetic means may be used to promote the movement of the beads into the receptacles 13. The first solvent 20 containing the beads 21 and 21' is introduced into the region 14 including the receptacles 13 in the step of beads introduction, followed by applying an external magnetic field to the beads 21 and 21' before or after introducing the second solvent 30 onto the first solvent 20 in the step. This can promote the movement of the beads 21 and 21' into the receptacles 13 by causing force towards the receptacles 13 to act on the beads 21 and 21'. The application of the magnetic field may be carried out, for example, by causing a magnet to near the opposite side of the side on which the receptacles 13 of the substrate 10 are provided (the bottom face side of the array 1).

The present embodiment enables to provide a large-area array including a large number of receptacles. For example, even with an array including one million or more receptacles, it is possible to efficiently seal the bead 21 or 21' into the receptacles so that any one of the beads 21 and 21' is stored in each of the receptacles. Thus, with the present embodiment, it is possible to detect the target molecules with high sensitivity, thereby enabling to detect the target molecules of such a quite low concentration as approximately 10 aM.

[Step of Deaeration]

The region 14 including the receptacles 13 of the substrate 10 may be made into an upper opened space as described above; however, when the region 14 is made into a closed space, a step of deaerating the inside of the region 14 may be carried out between the step of beads introduction and the step of beads storing. Preferably, the deaeration is carried out by, for example, a method of allowing the array 1 to stand still under reduced pressure. Specifically, the deaeration is carried out by, for example, a method of allowing the array 1 to stand still in a vacuum desiccator of approximately 0.1 atm for approximately 30 seconds.

The step of deaeration is not essential for the present invention. However, carrying out the step of deaeration removes the air in the receptacles 13, thereby making it possible to efficiently introduce into the receptacles 13 the beads 21 and 21'.

2. Method for Detecting Target Molecule

Next, the following describes the method for detecting the target molecule according to the present invention. The method for detecting a target molecule according to the present invention includes a step of reaction, a step of sealing beads, and a step of determination.

The present embodiment uses, as the beads, beads that specifically capture the target molecules. For example, each of such the beads may be the one having been bound to a molecule for specifically capturing the target molecule. Suitably used as the beads, the target molecule, and the molecule for specifically capturing the target molecule can be any of those exemplified in the above descriptions for the method for sealing beads.

The step of reaction is a step of reacting the beads with the target molecules. For example, the reaction between the beads and the target molecules can be carried out by mixing a solution containing the beads with a solution containing the target molecules.

The step of sealing beads is a step of carrying out the above-mentioned method for sealing beads by use of the beads which have been reacted with the target molecules in the step of reaction. Namely, the step of sealing beads is a step including the step of beads introduction and the step of beads storing, or a step including the step of beads introduction, the step of deaeration, and the step of beads storing. Note that descriptions of the step of beads introduction, the step of deaeration, and the step of beads storing are omitted here, since these steps can be carried out in the same manner as those described in the above section "Method for Sealing Beads".

The step of determination is a step of determining, after the step of sealing beads, whether or not each of the receptacles 13 contains any one of the beads 21' having captured the target molecules.

Suitable examples of the method of determining whether or not each of the receptacles 13 contains any one of the beads 21' having captured the target molecules encompass known molecular recognition reactions such as antigen-antibody reaction, streptavidin-biotin reaction, or complementary binding of nucleic acids. For example, this method can be a method of detecting a fluorescent material liberated from a fluorescent substrate when decomposed by a certain enzyme bound to (i) a target molecule or (ii) a molecule specifically bound to the target molecule. The detection of the fluorescent material is carried out by, for example, a method of determining a fluorescence intensity of each receptacle by use of, e.g., a fluorescence microscope or an image sensor.

In the step of determination, it is preferable to also determine whether each of the receptacles 13 contains any one of the beads 21 or any one of the beads 21'. The determination of whether each of the receptacles 13 contains any one of the beads 21 or any one of the beads 21' can be carried out by, for example, microscopic observation to determine the presence or absence of any one of the beads 21 or any one of the beads 21' in each of the receptacles 13.

Alternatively, the determination of the presence or absence of any one of the beads 21 or any one of the beads 21' in each of the receptacles 13 can be carried out by a method of detecting scattered light from the beads or a method of measuring an electric potential with a field-effect transistor (FET).

After the step of determination, based on (i) the number of receptacles 13 containing the beads 21 or the beads 21', and (ii) the number of receptacles 13 containing the beads 21' having captured the target molecules, it is possible to calculate a ratio of the number of beads having captured the target molecules with respect to the total number of beads. In this manner, it is possible to quantify a concentration of the target molecules.

According to the present embodiment, it is possible to provide a large-area array including a large number of receptacles; further, even with an array including one million or more receptacles, it is possible to efficiently seal the beads 21 or 21' into each of the receptacles. Thus, with the present embodiment, it is possible to detect the target molecules with high sensitivity, thereby enabling to detect the target molecules of such a quite low concentration as approximately 10 aM.

3. Array

Next, the following describes a configuration of the array 1 with reference to FIG. 1.

In the array 1, the substrate 10 includes a plate-like member 11 and the side wall 12 having a hydrophobic upper surface. The substrate 10 includes the plurality of receptacles 13 that are separated from each other by the side wall 12.

Preferably, the plate-like member 11 has a hydrophilic surface. The term "hydrophilic surface" refers to a surface whose affinity with a hydrophilic solvent is higher than that with a hydrophobic solvent. The plate-like member 11 may only needs to be made from a solid material. For example, the plate-like member 11 can be made from glass, silicon, or a polymer resin.

The side wall 12 is provided on the surface, preferably on the hydrophilic surface, of the plate-like member 11 and, separates the plurality of receptacles 13. The side wall 12 has the hydrophobic upper surface. The term "Hydrophobic" herein is used as a synonym for "lipophilic", and denotes a nature whose affinity with a hydrophobic solvent is higher than that with a hydrophilic solvent.

Note that the upper surface of the side wall 12 is preferably hydrophobic and the lateral surface thereof, i.e., an inner wall of each of the receptacles 13, may be either hydrophobic or hydrophilic.

For example, the side wall 12 may be made of a hydrophilic structure and a hydrophobic layer which is formed on an upper surface thereof. The hydrophilic structure may be made from, e.g., glass, silicon, or a polymer resin. The hydrophobic layer may be made from, e.g., a water repellent resin or a fluorocarbon polymer resin. Examples of the fluorocarbon polymer resin encompass amorphous fluorocarbon resin. The amorphous fluorocarbon resin is preferably used because of having a high hydrophobic property and having a low toxicity to a biological sample.

It is preferable to use, as the second solvent 30, a solvent having affinity to a hydrophobic layer forming the upper surface of the side wall 12 to an extent not dissolving the hydrophobic layer. A lower affinity to the hydrophobic layer of the second solvent 30 may inhibit layer substitution with the first solvent 20. Too high an affinity to the hydrophobic layer of the second solvent 30 may result in the dissolution of the hydrophobic layer and not enable the shape of the side wall 12 to be maintained. From such a viewpoint, a polymer having a perfluorocarbon structure (Fluorinert FC-40, Fluorinert FC-43, or the like) is preferably used as the second solvent 30 when the upper surface of the side wall 12 is formed of a fluorocarbon polymer resin.

Preferable examples of the amorphous fluorocarbon resin encompass at least one selected from CYTOP (Registered Trademark), TEFLON (Registered Trademark) AF2400, and TEFLON (Registered Trademark) AF1600. Among those, CYTOP (Registered Trademark) is most preferable because it is easy to be microfabricated.

Alternatively, the side wall 12 may be made from a hydrophobic material. For example, the side wall 12 may be made from a fluorocarbon polymer resin or a paraxylene polymer resin. Examples of the fluorocarbon polymer resin encompass an amorphous fluorocarbon resin. Preferably used as the amorphous fluorocarbon resin is any of those exemplified above.

The side wall 12 only needs to have such a configuration that the plurality of receptacles 13 are provided on the plate-like member 11. For example, the side wall 12 may be a plate-like structure parts of which corresponding to the receptacles 13 are holes.

A height of the side wall 12 measured from the surface of the plate-like member 11 (i.e., a thickness in a vertical direction) only needs to be designed so that one of the beads 21 and 21' once stored in the receptacles 13 would not be again discharged from the receptacles 13 during the step of beads storing. For example, the height of the side wall 12 may be designed so that most part of, preferably the whole part of, one of the beads 21 and 21' stored in one of the receptacles 13 is positioned lower than the upper surface of the side wall 12.

In order to efficiently store the beads 21 and 21' in the receptacles 13, the height of the side wall 12 is preferably equal to or greater than the average particle diameter of the beads 21 and 21'. Further, in order that only one of the beads 21 and 21' is stored in one of the receptacles 13, the height of the side wall 12 is preferably equal to or smaller than 1.5 times the average particle diameter of the beads 21 and 21'.

Each of the plurality of receptacles 13 is a recess capable of storing only one of the beads 21 and 21', and the plurality of receptacles 13 are separated from each other by the side wall 12. Each of the receptacles 13 has a bottom surface which is a part of the surface of the plate-like member 11, and the bottom surface is hydrophilic.

The receptacles 13 can have any shape or size, as long as the shape or size allows each of the receptacles 13 to store only one of the beads 21 and 21' therein. The region surrounded by the bottom surface and the lateral surface of each of the receptacles 13 may be shaped in, e.g., a circular cylindrical or a rectangular column.

A width "w" of each of the receptacles 13 in a horizontal direction (e.g., in a case where a cross section of each receptacle 13 when seen in the horizontal direction is shaped in a circle, the width "w" is a diameter of the circle; in a case where the cross section of each receptacle 13 when seen in the horizontal direction is shaped in a square, the width "w" is a length of one side of the square) only needs to be larger than the average particle diameter of the beads 21 and 21'. Preferably, the width "w" is, for example, 1 to 2 times larger than the average particle diameter of the beads 21 and 21'. In the present embodiment, each of the receptacles 13 has a depth equal to the height of the side wall 12. In order to efficiently store the beads in the receptacles, the depth of each of the receptacles of the present invention is preferably equal to or greater than the average particle diameter of the beads. Further, in order that only one of the beads is stored in one of the receptacles, the depth of each of the receptacles of the present invention is preferably equal to or smaller than 1.5 times the average particle diameter of the beads.

Techniques, such as photolithography, etching, and substrate lamination, for preparing the array 1 are the same as techniques for preparing general-purpose microchips and arrays.

According to the present embodiment, each of the receptacles 13 has a hydrophilic bottom surface, and the side wall 12 has a hydrophobic upper surface. Thus, the first solvent 20 containing the beads 21 and 21' can be efficiently introduced into the receptacles 13 when the hydrophilic first solvent 20 is used in the step of beads introduction. In addition, because the hydrophobic second solvent 30 used in the step of beads storing can be prevented from entering into the receptacles 13, the hydrophilic first solvent 20 in the receptacles 13 can be coated and hermetically sealed with the hydrophobic second solvent 30 to form droplets (liquid droplets).

The array 1 of the present embodiment may be, for example, an array including one million or more receptacles. Even with the array having such a large area, the use of the method for sealing beads of the present embodiment or the method for detecting a target molecule of the present embodiment makes it possible to efficiently seal the beads into the receptacles so that any one of the beads is stored in each of the receptacles. Thus, according to the present embodiment, it is possible to detect the target molecules with high sensitivity, thereby enabling to provide an array allowing detection of target molecules of such a quite low concentration as approximately 10 aM.

4. Kit

The array 1 and the beads 21 may be composed in the form of a kit. Each of the receptacles 13 in the arrays 1 is configured to be capable of storing only one of the beads 21 included in this kit.

Each of the beads 21 included in this kit may be the one specifically capturing the target molecule. For example, each of the beads 21 included in this kit may be the one having been bound to a molecule for specifically binding to the target molecule. Suitably used as the target molecule and the molecule for specifically binding to the target molecule can be any of those mentioned above.

This kit may further include a substance for specifically detecting the target molecule. Preferably used as the substance for specifically detecting the target molecule may be any of those mentioned above. Furthermore, the kit may further include, e.g., the first solvent and the second solvent.

5. Target Molecule Detection Device

Figure 2:
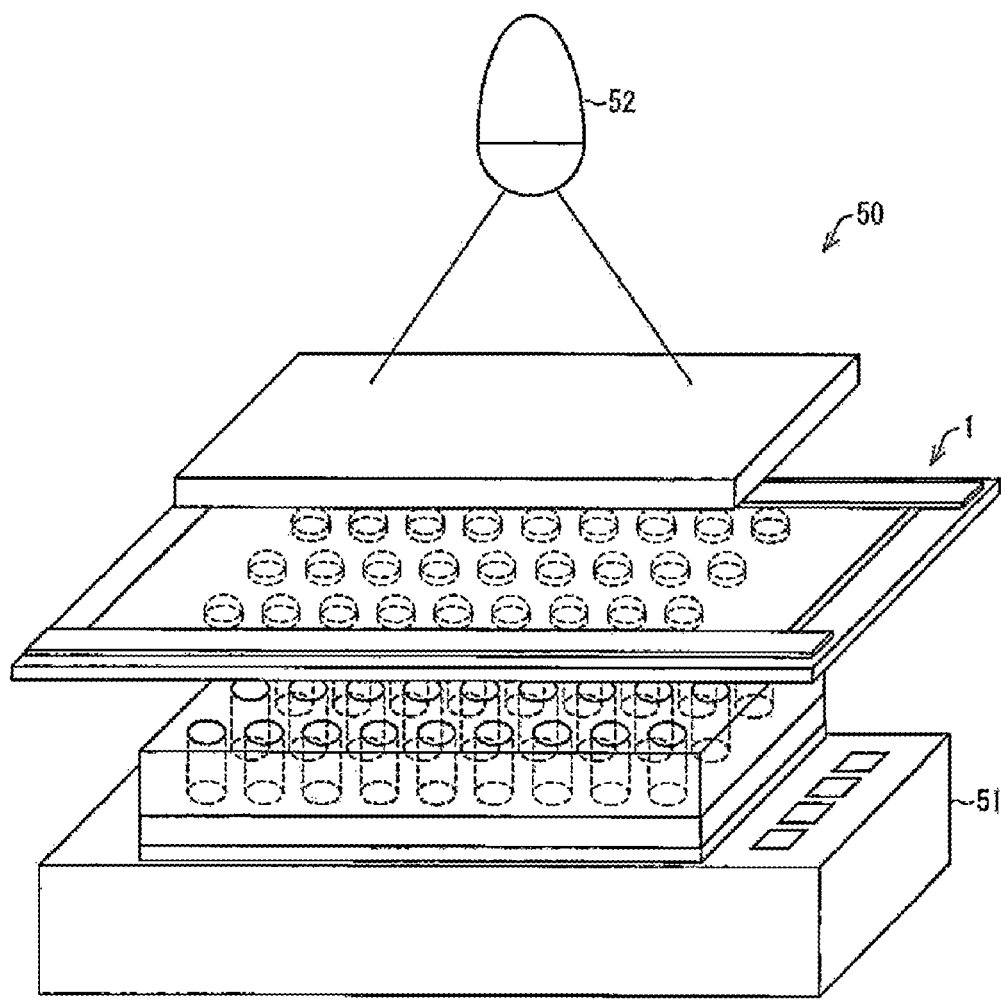
FIG. 2 is a view schematically illustrating one embodiment of a target molecule detection device according to the present invention.

Next, the following describes a target molecule detection device 50 of the present invention with reference to FIG. 2. FIG. 2 is a view schematically illustrating one embodiment of a target molecule detection device according to the present invention.

The target molecule detection device 50 according to the present embodiment includes the array 1, an image sensor 51, and a light source 52. Here, the array 1 is shown as a multi-well plate. Each well of the multi-well plate corresponds to the region 14 in FIG. 1. The composition of the array 1 is as described above and thus explanations of the array 1 are omitted here.

The image sensor 51 is a sensor for detecting light emitted by each of the receptacles 13 when the beads having captured the target molecules are stored in the receptacles 13. For example, the image sensor 51 may be a sensor for detecting fluorescence emitted by a fluorescent substrate when decomposed by a certain enzyme bound to (i) the target molecule or (ii) a molecule specifically bound to the target molecule. Suitably used as the image sensor 51 can be, for example, a CMOS image sensor.

The light source 52 is a light source for emitting light to the array 1. In FIG. 2, the light source 52 is provided above the array 1. However, the present invention is not particularly limited to this. Alternatively, the light source 52 may be the one emitting light to a lateral side of the array 1, for example.

Between the array 1 and the image sensor 51, an interference filter and/or a light guide array may be provided, for example. Further, between the light source 52 and the array 1, an excitation filter may be provided, for example.

According to the present embodiment, the array 1 and the image sensor 51 are directly connected with each other. This makes it possible to easily determine, without use of other device such as a microscope, whether or not any one of the beads having captured the target molecules is stored in each of the receptacles 13. This enables to carry out easy and high-speed detection of whether or not any one of the beads captured the target molecules is stored in each of the receptacles 13, and to provide the target molecule detection device at an affordable price.

6. Application Example of Method for Sealing Substance According to Present Invention In the method for sealing a substance according to the present invention, the substance sealed in the receptacles provided on the substrate may be beads, nucleic acid, protein, virus, cells, lipid membrane complex, or the like. In the above embodiment, the method has been described using beads as an example.

According to the present invention, the nucleic acid includes DNA and RNA. The protein and the virus include polymers (oligomers) thereof and complexes thereof with other substances. The cells include, particularly, bacterial cells, and the lipid membrane complex includes, particularly, liposome and exosome, and further cell organelle, such as mitochondria.

When the subject of sealing is nucleic acid, protein, virus, cells, lipid membrane complex, or the like, the method for sealing a substance according to the present invention can be used in applications, such as ELISA-PCR.

INDUSTRIAL APPLICABILITY

The present invention is suitably applicable to a method for detecting target molecules of low concentration, an array therefor, a device therefor, and the like.

REFERENCE SIGNS LIST

1: Array
10: Substrate
11: Plate-like Member
12: Side Wall
13: Receptacle
14: Region
20: First Solvent
21, 21': Beads
30: Second Solvent

The invention claimed is:

1. A method for sealing a substance in a receptacle, the method comprising:
(i) a step of introducing a hydrophilic solvent containing the substance and a surfactant on a substrate, wherein the substrate has a hydrophilic surface,
a container wall extends above the substrate,
the surface of the substrate and the container wall form an opened well,
a plurality of receptacles capable of storing the substance are formed, separated from each other by a side wall, on the hydrophilic surface of the substrate, and the side wall has a hydrophobic upper surface; and (ii) a step of introducing a hydrophobic solvent having a greater specific gravity than that of the hydrophilic solvent onto the hydrophilic solvent so that the hydrophobic solvent moves down below the hydrophilic solvent due to its greater specific gravity than that of the hydrophilic solvent and thereby the hydrophilic solvent is substituted by the hydrophobic solvent, thereby to form droplets of the hydrophilic solvent within the plurality of receptacles covered with the hydrophobic solvent, the step (ii) being carried out after the step (i); wherein the hydrophobic solvent is introduced on the hydrophilic solvent from the opening of the opened well, and at least one of the droplets of the hydrophilic solvent formed within the plurality of receptacles covered with the hydrophobic solvent contains the substance.

2. The method as set forth in claim 1, wherein the surfactant is polyoxyethylene sorbitan monolaurate or polyethylene glycol mono-4-octylphenyl ether.

3. The method as set forth in claim 1, wherein the surfactant has a concentration of 0.01% by weight to 1% by weight.

4. The method as set forth in claim 1, wherein the hydrophobic solvent is at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixed solvent that includes at least one of these solvents.

5. The method as set forth in claim 1, wherein the hydrophilic solvent is at least one selected from the group consisting of water, hydrophilic alcohol, hydrophilic ether, ketone, nitrile solvents, dimethyl sulfoxide, and N,N-dimethylformamide, or is a mixed solvent that includes at least one of these solvents.

* * * * *